United States Patent [19]

Lundquist

[11] 4,079,736

[45] Mar. 21, 1978

[54] COMBINATION DRUG ADMINISTRATION DEVICE AND ALARM SYSTEM AND METHOD

[75] Inventor: Ingemar H. Lundquist, Oakland, Calif.

[73] Assignee: Valleylab, Boulder, Colo.

[21] Appl. No.: 689,113

[22] Filed: May 24, 1976

[51] Int. Cl.² ............................................. A61M 5/14
[52] U.S. Cl. ............................. 128/214 R; 128/214 E; 137/556; 222/39; 222/49; 340/282
[58] Field of Search .................... 340/282; 128/214 R, 128/214 C, 214 E, 214 F, 218 C, 218 A, DIG. 12, DIG. 13; 222/39, 47, 49; 137/554, 556

[56] References Cited

U.S. PATENT DOCUMENTS

| | | | |
|---|---|---|---|
| 1,410,530 | 3/1922 | Larche | 128/220 |
| 2,761,445 | 9/1956 | Cherkin | 128/214 F |
| 2,865,371 | 12/1958 | Dorbecker et al. | 128/214 F |
| 3,425,415 | 2/1969 | Gordon et al. | 128/214 E |
| 3,543,752 | 12/1970 | Hesse et al. | 128/230 X |
| 3,884,228 | 5/1975 | Hahn | 128/214 F |
| 3,965,897 | 6/1976 | Lundquist | 128/214 R |

*Primary Examiner*—Dalton L. Truluck
*Attorney, Agent, or Firm*—Flehr, Hohbach, Test, Albritton & Herbert

[57] ABSTRACT

The combination drug administration device and alarm system is adapted to be connected to a source of intravenous liquid and to a patient. A container is provided having a inlet and an outlet. A piston is slidably mounted in the container for movement between extended and retracted positions. A stem is secured to the piston and has a portion thereof remaining out of the container during movement between the extended and retracted positions. A switch is provided and is mounted on the stem exterior of the container so that the switch means can be slidably positioned on the stem and will be retained on the stem in an adjusted predetermined position thereon but which will not impede movement of the piston and the stem in the container. The switch has an operating member adapted to be engaged by the container as the piston and the stem move as liquid is being dispensed from the container to cause actuation of an alarm when a predetermined quantity of liquid has been dispensed from the container which is less than the total amount of liquid in the container.

The method is for administering a drug in an intravenous liquid from a source of intravenous liquid to a patient by the use of the container having an inlet and an outlet with a piston slidably mounted in the container and a stem secured to the piston and extending out of the container. A predetermined amount of the intravenous liquid is provided in the container and a drug is mixed into the liquid in the container. The liquid with the drug therein is then dispensed to the patient through the outlet. An alarm is initiated when a predetermined amount less than the total amount of the liquid in the container has been dispensed to the patient to provide a pre-alarm.

4 Claims, 3 Drawing Figures

U.S. Patent    March 21, 1978    4,079,736
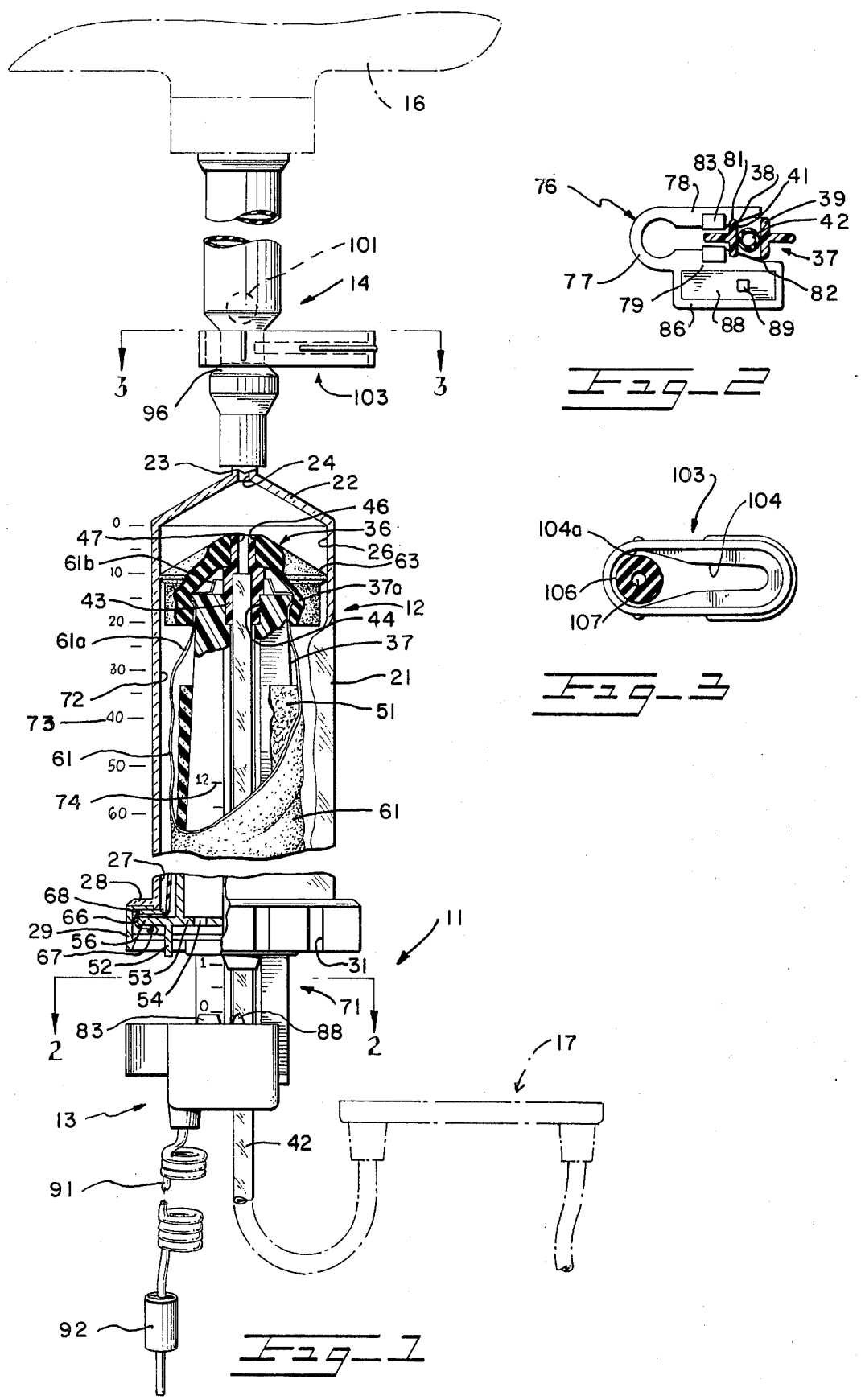

COMBINATION DRUG ADMINISTRATION DEVICE AND ALARM SYSTEM AND METHOD

BACKGROUND OF THE INVENTION

In copending application Ser. No. 514,219 filed on Oct. 11, 1974 now U.S. Pat. No. 3,965,897 there is disclosed a measured volume drug administration device for use with an intravenousfeeding pump. This device is utilized for mixing drugs into an intravenous liquid so that the drug can be injected into the patient at the same time that the intravenous liquid is being introduced. It has been found that in the use of such a device it is desirable to provide a pre-alarm when a predetermined amount of liquid has been dispensed as selected by the nurse or attendant so that the condition of the patient can be observed prior to administration of all of the drug which has been introduced into the device. No means for giving such a pre-alarm is provided in the device disclosed in the said copending application Ser. No. 514,219 filed on Oct. 11, 1974. There is therefore a need for a pre-alarm device to be utilized in connection with a drug administration device of the type disclosed in the said copending application Ser. No. 514,219 filed on Oct. 11, 1974.

SUMMARY OF THE INVENTION AND OBJECTS

The combination drug administration device and alarm system is adapted to be connected to a source of intravenous liquid and a patient for dispensing the intravenous liquid to the patient. A container having an inlet and an outlet is provided. A piston is slidably mounted in the container for movement between extended and retracted positions in the container. A stem is secured to the piston and has a portion thereof extending out of the container and which remains out of the container during movement of the piston between the extended and retracted positions. Switch means is provided for a pre-alarm. Means is provided for mounting the switch means on the stem exterior of the container so that said switch means can be slidably positioned on said stem and will be retained on said stem and in an adjustable pre-determined position but which will not impede the movement of said piston and said stem. The switch means has an operating member adapted to come into engagement with the container upon movement of said piston and said stem as liquid is dispensed from said container to the patient to initiate an alarm.

In general, it is an object of the present invention to provide a combination drug administration device and alarm system which makes it possible to provide a pre-alarm, that is, an alarm that is prior to the time when all the liquid in the drug administration device having the drug therein has been dispensed to the patient.

Another object of the invention is to provide a combination device and alarm system of the above character in which the pre-alarm can be readily removed when it is not desired.

Another object of the invention is to provide a device and alarm system of the above character in which the alarm system can be very readily placed on the drum administration device.

Another object of the invention is to provide a combination device and alarm system of the above character in which the alarm device can be readily positioned to give an alarm at different quantites of dispensed liquid.

Another object of the invention is to provide a combination device and alarm system of the above character in which the alarm does not impede the operation of the drug administration device.

Another object of the invention is to provide a combination device and alarm system of the above character in which the alarm system can be readily removed from the device when it is not required.

Another object of the invention is to provide a device and alarm system of the above character in which the alarm system can be readily placed upon the device and readily removed from the device.

Another object of the invention is to provide a combination device and alarm system of the above character in which the alarm system can be readily positioned to provide an alarm at an adjustable position.

Additional objects and features of the invention will appear from the following description in which the preferred embodiment is set forth in detail in conjunction with the accompanying drawings.

BRIEF DESCRIPTION OF THE DRAWINGS

FIG. 1 is a side elevational view partially in cross-section of a combination drug administration device and alarm system incorporating the present invention and showing in broken lines, an IV bottle and a pump with which it is used.

FIG. 2 is a cross-sectional view taken along the line 2—2 at FIG. 1.

FIG. 3 is a cross-sectional view taken along the line 3—3 of FIG. 1.

BRIEF DESCRIPTION OF THE PREFERRED EMBODIMENT

The combination drug administration device and alarm system 11 as shown in FIG. 1 of the drawings includes a drug administration device 12 of the type described in copending application Ser. No. 514,219 filed on Oct. 11, 1974, now U.S. Pat. No. 3,965,897. It also consists of an alarm system 13 which is adaptedly to be mounted upon the drug administration device 12 as hereinafter described. The drug administration device 12 is adaptedly to be connected to a universal drip chamber and spike assembly 14 of the type described in copending application Ser. No. 689,114 filed on May 24, 1976. The drip chamber and spike assembly 14 has been inserted into a bottle 16 shown in broken lines which serves as a source of intravenous liquid to be utilized in connection with the drug administration device 12 for supplying to a patient. The drug administration device 12 is also adaptedly to be connected to a pump 17 of the type described in copending application Ser. No. 689,115 filed May 24, 1976 to supply intravenous liquid to the patient. The pump 17 can be a flow-through device or can supply the intravenous liquid at a controlled rate under the control of the controller as described in said copending application Ser. No. 689,115 filed May 24, 1976.

The drug administration device 12 as described in said copending application Ser. No. 514,219 filed on Oct. 11, 1974, now U.S. Pat. No. 3,965,897 consists of a cylindrical housing or container 21 which is provided with an upper conical end 22 that has a centrally disposed inlet fitting 23 formed integral therewith. The fitting 23 is provided with an inlet flow passage 24 which is in communication with a mixing chamber 26 provided within the container 21. The container 21 is provided with an open end 27. It is provided with a radially extending flange 28 which has a downwardly extending rim 29 formed integral therewith. The rim is provided with a plurality of circumferentially-spaced slots 31 which open downwardly through the lower extremity of the rim 29.

The piston 36 is mounted for sliding movement within the cylinder 26. The piston is formed of a suitable relatively soft resilient and flexible material such as rubber. The piston 36 is carried by a stem 37. The stem 37 is of such a length so that it extends out of the container 26 and has a portion thereof which remains outside of the container regardless of the position of the piston 36. The stem 37 is provided with two longitudinally extending portions 38 and 39 which are T-shaped in cross-section as can be seen from FIG. 2. The T-shaped portions 38 and 39 are interconnected at their upper ends. A space 41 is provided between the portion 38 and 39 and is of a size to accommodate a flexible plastic outlet tube 42. The stem 37 is formed of a suitable material such as plastic and has its upper end terminating in a disc-like portion 37a.

The upper end of the tube 42 is mounted in a fitting 43 which has its lower end mounted in a hole 44 provided in the disc-like portion 37a. The upper end of the fitting 43 is mounted in a hole 46 provided in the piston 36. The fitting 43 is provided with a flow passage 47 which is in communication with the interior of the tube 42. It also opens into the mixing chamber 26.

A cylindrical member 51 formed of a relatively flexible material such as foam plastic is mounted over the stem 37. The lower extremity of the cylindrical member 51 is within a ring 52. The ring 52 is provided with an inwardly extending flange 53 which is adapted to support the lower extremity of the conical member 51. The ring 52 is mounted on the stem 52. The flange 53 is provided with two cut-outs 54 which are adapted to receive the T-shaped portions 38 and 39. The ring 52 is also provided with an outwardly extending flange 56 which is adapted to frictionally engage the rim 29 as hereinafter described.

A germ barrier is provided within the container 21 for preventing any contamination from coming in contact with the exterior wall of the container 26. The germ barrier takes the form of a sheath or diaphragm 61 which is generally cylindrical in shape that is adapted to fit over the stem 37 and the resilient cylindrical member 51. The sheath or diaphragm 61 is provided with an upper conical portion 61 which is adapted to fit over the top of the disc-like portion 37a of the stem and has a small generally cylindrical portion 61b which is adapted to fit tightly over the fitting 43. The upper end of the sheath or diaphragm 61 including a portion of the conical portion 61a is adapted to be clamped tightly over the disc-like portion 37a by the rubber piston 36 which is slipped on to the fitting 43 and over the top of the disc-like portion of the stem 37 to firmly clamp the sheath and membrane 61 to the piston and to form a tight seal between the same.

As can be seen from FIG. 1, the upper end of the piston 36 is generally conical as shown. The piston 36 is provided with an annular lip 63 which is formed integral therewith and which is relatively flexible and tightly engages the sidewall of the container 21.

The lower extremity of the sheath or diaphragm 61 is stretched over a rigid disc 66 as shown in FIG. 1 which overlies the flange or collar 56 provided on the ring 52. The sheath or diaphragm 61 is provided with a bead 67 which lies between the washer or ring 66 so as to form a good seal between the washer or ring 66 and the collar or flange 56.

Hydrophobic filter means is provided in the form of an annulus 68 formed of a suitable hydrophobic material. The annulus overlies a portion of the sheath or diaphragm 61 which is stretched over the washer or ring 66 and has its upper surface engaging the flange 28.

The entire stem assembly 71 consisting of the stem 37 with all the parts carried thereon including the cylindrical member 51 and the sheath or diaphragm 61 after assembly can be readily inserted into the mixing chamber 26 by pressing the piston 36 upwardly into the chamber. The cylindrical member 51 is pushed firmly up into the rim 29 so it frictionally engages same and clamps the lower extremity of the sheath or diaphragm 61 firmly in place as well as the hydrophobic filter 68. When this is the case, air can only enter into the space below the piston 36 within the chamber 26 through the slots 31 and through the hydrophobic filter material 68 to the space 72 below the piston. This completes the general description of the drug administration device.

The container 21 is provided with appropriate indicia 73, as for example, indicia indicating millilitres or cubic centimeters of liquid within the chamber 26 above the piston 36 with the lip 63 serving as the member to be observed in conjunction with the indicia 73. In addition the T-shaped members 38 and 39 are provided with indicia 74, as for example, from 1 to 10 with 0 being in registration with the upper extremity of the actuator button 89 when the alarm system 13 is in its lowermost position on the stem 37.

The alarm system 13 consists of a U-shaped clamping member 76 which is formed of a suitable material having spring-like characteristics, as for example, Delrin. The U-shaped clamping member 76 is provided with a bight 77 and first and second legs 78 and 79. The legs 78 and 79 are provided with vertically-extending slots 81 which face each other and which are adapted to receive opposing portions of one of the T-shaped portions 38 and 39 of the stem 37 as can be seen from FIG. 2. The legs 78 and 79 are also provided with inclined surfaces 82 which facilitate camming the legs 78 and 79 over the T-shaped portion until the T-shaped portion comes into engagement with the slot 81 Projections 83 are formed on the legs 78 and 79 and serve as markers or indicators for reading the indicia 74 on the stem 37. If desired, to increase the friction between the U-shaped clamping member 76 and the stem 37, a friction material, as for example, a small pad of felt (not shown) can be cemented into the slots 81. A receptacle 86 is formed integral with the leg 79 and has an upper open end which is adapted to receive a small microswitch of a conventional type in such a manner so that the upper surface of the microswitch is flush with the upper surface of the receptable 86. The microswitch is provided with operating member 89. The microswitch 88 with its operating member 89 is positioned in such a manner so that when the U-shaped clamping member 76 is secured to the stem, the operating member 89 is adapted to be engaged by the lower extremity of the ring 52. The operating arm 89 operates contacts with the microswitch to establish a contact closure or a contact opening depending upon the type of switch utilized. The microswitch is connected to the cord 91. The cord 91 is connected to a jack 92 which is adapted to be connected into the controller to actuate an alarm, when the actuator 89 is engaged as hereinafter described.

The flexible outlet tube is adapted to be connected into the inlet of the pump 17 which as hereinbefore explained is of the type described in copening application Ser. No. 689,115 filed May 24, 1976.

The inlet fitting 23 is provided on the drug administration device 12 is adaptedly to be mounted in the lower extremity of the universal drip chamber and spike assembly 14 which has also been identified as the type described in copending application Ser. No. 689,114 filed May 24, 1976. As disclosed therein, it includes an injection site 96. It also includes a ball-like float 101 which is adapted to seat within a valve seat provided within the drip chamber to establish a seal to prevent any further air from entering into the drug administration device 12.

A clamping device 103 for accomplishing the same function is mounted on the lower extremity of the drug chamber and spike assembly 14. The clamping device 103 can be formed of a suitable material such as plastic. It is provided with an elongate slot 104 extending longitudinally thereof. The slot 104 is provided with an enlarged generally circular portions 104a, a tapered portion 104b and a narrower tapered portion 104c. The drip chamber and spike assembly 14 includes a narrow tubular portion 106 having a flowpassage 107 therein. As can be seen, when the clamping device 103 is moved from the right to the left as viewed in FIG. 4, the resilient tubular portion 106 will be clamped by the narrower portions 104b and 104c of the clamping device 103 to close off or occlude the passage 107.

Operation of the combination drug administration device and alarm system in performing the present method may now be briefly described as follows. The operation of the drug administration device 12 is generally described in copending application Ser. No. 514,219 filed on Oct. 11, 1974, now U.S. Pat. No. 3,965,897. Let it be assumed that the drip chamber and spike assembly 14 has been inserted into a bottle 16 and that the drip chamber has been filled with liquid. Thereafter, the clamping device 103 may be moved to the right as viewed in FIG. 4 to permit liquid to pass from the drip chamber into the drug administration device 12. Liquid is introduced into the chamber 26 by withdrawing the stem 37 which causes withdrawal of the piston 36. This withdrawal is accomplished by manually grasping the stem to withdraw the piston until the amount of liquid desired has been drawn into the chamber 26.

When the appropriate amount of liquid has been introduced into the chamber 26 as can be ascertained by the operator observing the indicia 73 provided on the container 21, the clamping device 103 is moved to the left as viewed in FIG. 4 to close off the container 21 from the source of intravenous liquid. The drug to be administered to the patient can be then introduced by hypodermic needle through the injection site 96. The introduction of the drug into the chamber 26 will cause a further lowering of the piston 36 within the container 21. Thus, for example, if 2 cc. of the drug are mixed with 20 cc. of fluid already in the container 26, the addition of the 2 cc. will cause the piston to move down to 22 cc.

Now let it be assumed that it is desired to initiate a pre-alarm condition to alert the nurse when one-half of the intravenous liquid with the drug therein has been dispensed to the patient. The nurse or attendant will take one of the alarm devices 13 and slide it onto the stem 37 so that the slots 81 are in engagement with one of the T-shaped members 38 or 39. It is thereafter slidably adjusted longitudinally of the stem 37 to the desired position to give an alarm at the appropriate time. For example, if the nurse wishes to have an alarm initiated when one-half of the liquid has been dispensed to the patient, it is merely necessary to adjustably position the switch assembly 13 on the stem one-half of the distance between 0 and the number which is exposed. The jack 92 is placed in the controller (not shown) and the controller is placed in operation to start the operation of the pump 17 assuming that the pump has been properly filled as described in copending application Ser. No. 689,115 filed May 24, 1976.

As soon as the pump is placed in operation, liquid will be taken from the chamber 26 through the passage 47 and through tube 42 and into the pump and thence to the patient. As liquid is withdrawn from the chamber 26, atmospheric pressure will cause the piston to rise in the chamber and to follow the liquid as it is removed from the chamber 26. As the piston 36 moves upwardly, the stem 37 moves upwardly with it as does the alarm device 13 which is mounted upon the stem 37. This action continues until the operating button 89 comes into engagement with the lower extremity of the collar or ring 52. As soon as this occurs, a circuit function is initiated, as for example, a circuit closure or a circuit opening to initiate an alarm to the controller. This can be a visual or audible alarm to inform the nurse that the desired amount of liquid has been introduced into the patient.

It should be appreciated that the initiation of this alarm which shall be called a pre-alarm does not affect the continued operation of the device. The pump 17 can still continue to pump liquid from the chamber 26 in the piston 36 and will continue to move upwardly in the chamber. The stem 37 will follow the piston. The alarm device 13 which is mounted on the stem will remain in engagement with the ring or collar 52 but will permit relative sliding movement between the alarm device 13 and the stem 37 so as not to impede administration of the intravenous liquid with the drug therein to the patient.

Thus, it can be seen that the frictional engagement between the alarm device 13 and the stem 37 is sufficient so that the alarm device 13 will ride with the stem 37 to cause operation of the actuator button 89 when it strikes the ring or collar 52 but that it is insufficient to impede further upward movement of the stem 37 and the piston 36 under the influence of the pump 17 withdrawing liquid from the chamber 26. The pump 17 can continue to operate to remove all the liquid from the chamber 26. As soon as all the liquid has been exhausted from the chamber 26, another alarm at the control will be energized indicating that a negative pressure condition exists. This will also inform the nurse or attendant that all of the liquid with the drug therein has been dispensed to the patient. Thereafter, if it is desired to continue the delivery of intravenous liquid to the patient, the clamping device 103 can be moved to the right as shown in FIG. 4 to permit intravenous liquid to enter the drug administration device and to permit the IV liquid to enter the passage 47 and the tube 42 to be delivered to the patient. It can be seen that this can be accomplished without disconnecting the drug administration device 36 from the patient. Thereafter the same device can be utilized for administering additional drugs to the patient, if desired.

With the foregoing construction, it is possible for the nurse or attendant to provide a pre-alarm under various conditions. When a pre-alarm is not required or not necessary, the alarm device 13 can be readily removed from the stem 37. If it is again desired to utilize the same, the alarm device 13 can be readily mounted on the stem and then adjusted to the desired position.

In the drug administration device, the construction is such so that the sidewalls of the container 21 will not be contaminated. The cylindrical foam material 51 prevents pinching of the sheath or diaphragm 61 when the piston 36 is being lowered by retraction of the stem 37. The hydrophobic filter ensures that any air entering into the space 72 will be filtered.

it is apparent from the foregoing, that there has been provided a combination drug administration device and alarm system in which it is possbile to readily set a pre-alarm by adjustment of the alarm device. The alarm device can be readily placed in operation and also readily removed when desired. The alarm device is relatively simple in construction in that it can be readily connected to the controller.

What is claimed is:

1. In a combination drug administration device and alarm system adapted to be connected to a source of intravenous liquid and a patient, a container having an inlet and an outlet, a piston slidably mounted in the container for movement between extended and retracted positions, a stem secured to said piston and having a portion thereof remaining out of said container during movement between said extended and retracted positions, a switch means and means for mounting said switch means on said stem exterior of the container so that said switch means is carried solely by said stem and so that said switch means can be slidably positioned on the said stem and will be retained on said stem in a predetermined adjustable position but which will not impede movement of said stem and the piston carried thereby, said switch means having an operating member adapted to be engaged upon longitudinal movement of said piston and stem by relative movement between said stem and said container to indicate when a predetermined quantity of liquid remains in the container.

2. In a combination drug administration device and alarm system adapted to be connected to a source of intranveous liquid and a patient, a container having an inlet and an outlet, a piston slidably mounted in the container for movement between extended and retracted positions, a stem secured to said piston having a portion thereof remaining out of said container during movement between extended and retracted positions, a germ barrier disposed within the container and secured to said piston and said container to prevent contamination of the inner wall of said container, means within the germ barrier for preventing pinching of said germ barrier in said container, switch means and means for mounting said switch means on said stem exterior of the container so that said switch means can be slidably positioned on said stem and will be retained on said stem in a predetermined adjustable position but which will not impede movement of said stem and the piston carried thereby, said switch means having an operating member adapted to be engaged upon longitudinal movement of said piston and stem by relative movement between said stem and said container to indicate when a predetermined quantity of liquid remains in the container.

3. A combination drug administration device and alarm system as in claim 2 wherein a space is provided between the germ barrier and the interior of the container together with hydrophobic filter means for filtering air entering said space.

4. In a method for administering a drug in an intravenous liquid from a source of intravenous liquid to a patient by the use of a container having an inlet and an outlet with a piston slidably mounted in the container and a stem secured to the piston and extending out of the container, filling the container with a desired amount of intravenous liquid, introducing a drug into the liquid in the container so that the drug is mixed into the liquid in the container, dispensing the liquid from the container to the patient, providing a switch means solely on the stem at a predetermined position which is actuated with a predetermined relative movement between the switch means and the container which represents less than the total relative possible movement between the switch means and the container and initiating an alarm in response to actuation of the switch means when a predetermined amount less than to total of the liquid with the drug mixed therein has been dispensed to the patient.

* * * * *